United States Patent
Orban et al.

(10) Patent No.: US 7,666,230 B2
(45) Date of Patent: Feb. 23, 2010

(54) IMPLANT DEVICE FOR CARTILAGE REGENERATION IN LOAD BEARING ARTICULATION REGIONS

(75) Inventors: Janine M. Orban, Warsaw, IN (US); Herbert E. Schwartz, Fort Wayne, IN (US); Nathaniel W. Grobe, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 522 days.

(21) Appl. No.: 10/730,423

(22) Filed: Dec. 8, 2003

(65) Prior Publication Data

US 2005/0125073 A1 Jun. 9, 2005

(51) Int. Cl.
*A61F 2/30* (2006.01)
(52) U.S. Cl. .............................. 623/23.58; 623/23.75
(58) Field of Classification Search ............. 623/23.58, 623/23.75, 23.76, 13.11, 13.12, 13.14, 13.18, 623/14.2; 606/60, 72, 75, 76, 77, 232
See application file for complete search history.

(56) References Cited

U.S. PATENT DOCUMENTS

| | | | |
|---|---|---|---|
| 5,062,850 A | | 11/1991 | MacMillan |
| 5,116,374 A | | 5/1992 | Stone |
| 5,306,311 A | | 4/1994 | Stone et al. |
| 5,624,463 A | | 4/1997 | Stone et al. |
| 5,679,723 A | | 10/1997 | Cooper et al. |
| 5,713,374 A | | 2/1998 | Pachence et al. |
| 5,747,390 A | | 5/1998 | Cooper et al. |
| 5,769,899 A | * | 6/1998 | Schwartz et al. .............. 606/77 |
| 5,919,234 A | | 7/1999 | Lemperle et al. |
| 6,080,194 A | | 6/2000 | Pachence et al. |
| 6,371,958 B1 | | 4/2002 | Overaker |
| 6,387,693 B2 | | 5/2002 | Rieser et al. |
| 6,444,222 B1 | | 9/2002 | Asculai et al. |
| 6,451,059 B1 | | 9/2002 | Janas et al. |

(Continued)

FOREIGN PATENT DOCUMENTS

DE 94 13 778 1/1996

(Continued)

OTHER PUBLICATIONS

Grigolo, Brunella et al.,"Transplantation of Chondrocytes Seeded on a Hyaluronan Derivative (Hyaff®-11) into Cartilage Defects in Rabbits", Biomaterials, © 2001, Elsevier Science Ltd., pp. 2417-2424; 2001.

(Continued)

*Primary Examiner*—Eduardo C Robert
*Assistant Examiner*—David Comstock
(74) *Attorney, Agent, or Firm*—Maginot, Moore & Beck LLP

(57) ABSTRACT

An implant device for cartilage regeneration in loading-bearing regions uses the osteochondral defect model. The implant is formed of resorbable polymeric materials. The implant is designed such that load is transmitted from the articulating surface of the bone platform through the implant to the entire area of subchondral bone of the bone platform. Application of load in this manner results in reduced subchondral bone resorption, leading to joint stabilization and maintenance of normal joint biomechanics. The implant allows for the incorporation therein of a resorbable scaffold or matrix material. The present implant solves the current inability to regenerate cartilage in load-bearing articulating surfaces using engineered scaffold devices.

6 Claims, 11 Drawing Sheets

U.S. PATENT DOCUMENTS

| | | |
|---|---|---|
| 6,511,511 B1 | 1/2003 | Slivka et al. |
| 6,530,956 B1 | 3/2003 | Mansmann |
| 6,575,986 B2 | 6/2003 | Overaker |
| 6,602,294 B1 | 8/2003 | Sittinger et al. |
| 2001/0014473 A1 | 8/2001 | Rieser et al. |
| 2001/0016353 A1 | 8/2001 | Jannas et al. |
| 2001/0039455 A1 | 11/2001 | Simon et al. |
| 2002/0082694 A1 | 6/2002 | McKay |
| 2002/0090391 A1 | 7/2002 | Geistlich et al. |
| 2002/0119177 A1 | 8/2002 | Bowman et al. |
| 2002/0120274 A1 | 8/2002 | Overaker et al. |
| 2002/0139147 A1 | 10/2002 | Janas et al. |
| 2002/0173855 A1 | 11/2002 | Mansmann |
| 2003/0003127 A1 | 1/2003 | Brown et al. |
| 2003/0003153 A1 | 1/2003 | Asculai et al. |
| 2003/0004578 A1 | 1/2003 | Brown et al. |
| 2003/0033021 A1 | 2/2003 | Plouhar et al. |
| 2003/0075822 A1 | 4/2003 | Slivka et al. |
| 2003/0083665 A1 | 5/2003 | Re et al. |
| 2003/0095994 A1 | 5/2003 | Geistlich et al. |
| 2003/0108587 A1 | 6/2003 | Orgill et al. |

FOREIGN PATENT DOCUMENTS

| | | |
|---|---|---|
| EP | 0 324 852 B1 | 7/1989 |
| EP | 0 461 201 B1 | 12/1991 |
| EP | 1 129 675 A2 | 9/2001 |
| EP | 1 216 669 | 6/2002 |
| EP | 1 234 552 A1 | 8/2002 |
| EP | 1 270 025 A2 | 1/2003 |
| EP | 1 277 450 A3 | 1/2003 |
| EP | 1 366 718 | 12/2003 |
| WO | WO 90/09769 | 9/1990 |
| WO | WO 96/24304 | 8/1996 |
| WO | WO 96/24310 | 8/1996 |
| WO | WO 97/45147 | 12/1997 |
| WO | WO 98/07384 | 2/1998 |
| WO | WO 98/51317 | 11/1998 |
| WO | WO 98/53768 | 12/1998 |
| WO | WO 00/45870 | 8/2000 |
| WO | WO 00/45871 | 8/2000 |
| WO | WO 00/47244 | 8/2000 |
| WO | WO 00/74554 | 12/2000 |
| WO | WO 01/02030 A2 | 1/2001 |
| WO | WO 01/30276 | 5/2001 |
| WO | WO 01/32072 A2 | 5/2001 |
| WO | WO 02/064180 | 8/2002 |
| WO | WO 02/070030 A1 | 9/2002 |
| WO | WO 02/071985 A1 | 9/2002 |
| WO | WO 03/007787 A2 | 1/2003 |
| WO | WO 03/007879 A2 | 1/2003 |

OTHER PUBLICATIONS

Jackson, D.W. et al.,"Spontaneous Repair of Full-Thickness Defects of Articular Cartilage in a Goat Model", The Journal of Bone & Joint Surgery, vol. 83-A, No. 1, Jan. 2001, pp. 53-64.

Breinan, H.A. et al., "Effect of Cultured Autologous Chondrocytes on Repair of Chrondral Defects in a Canine Model", Journal of Bone and Joint Surgery-American, Oct. 1997, vol. 79-A, No. 10, pp. 1439-1451.

* cited by examiner

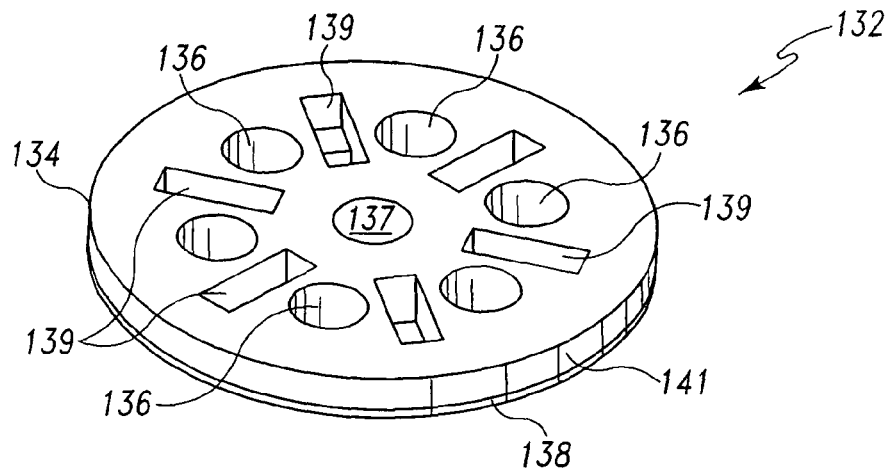
Fig. 16
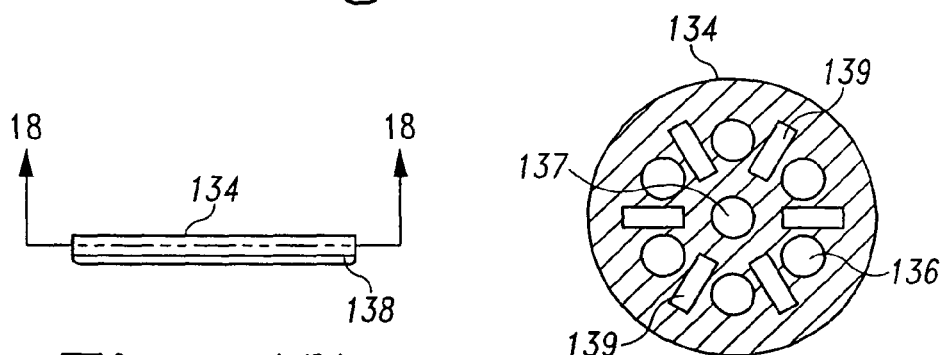
Fig. 17
Fig. 18
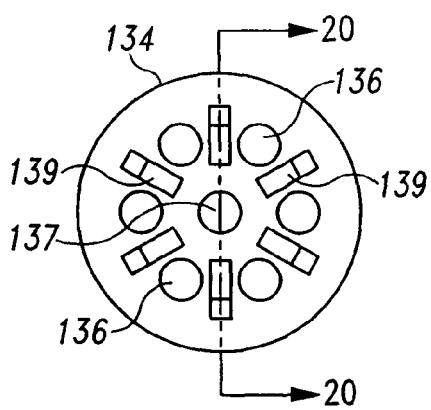
Fig. 19
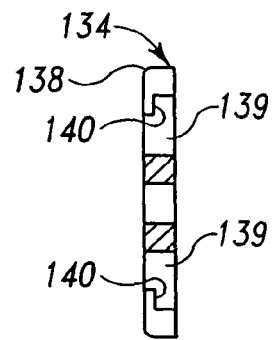
Fig. 20

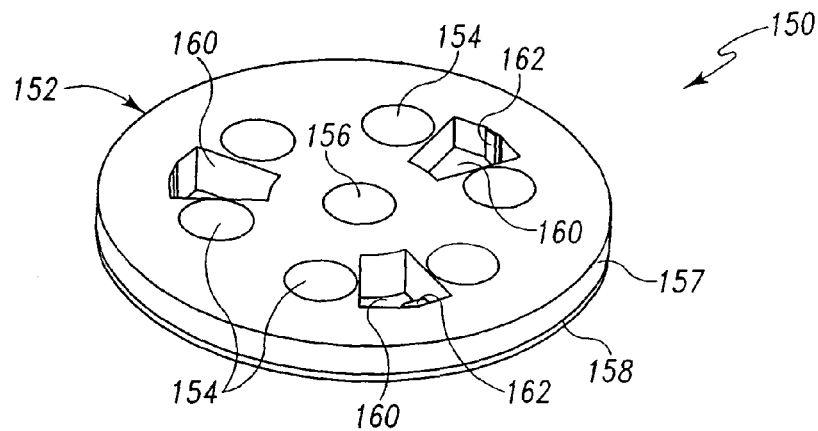
Fig. 21
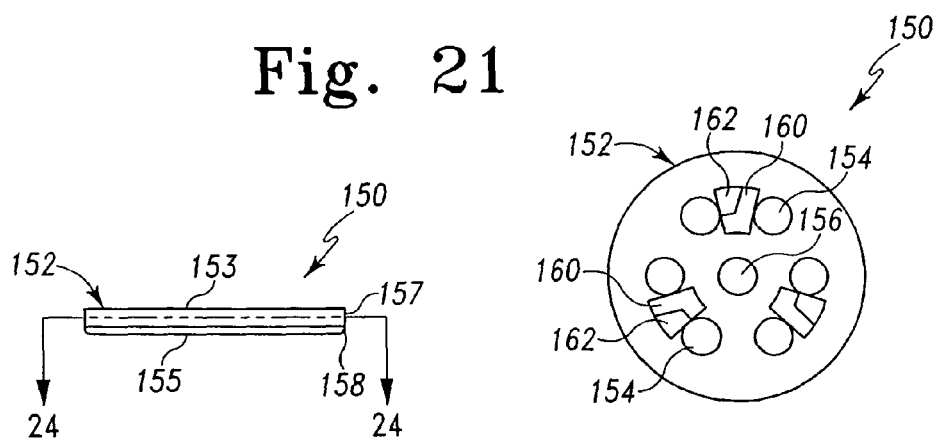
Fig. 23
Fig. 22
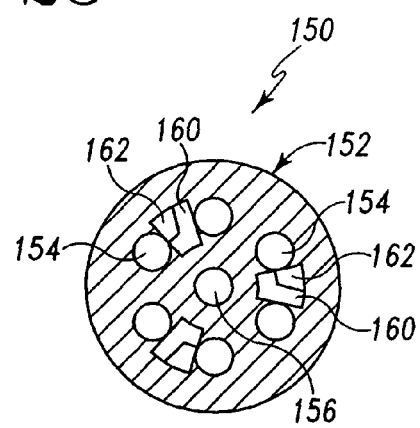
Fig. 24

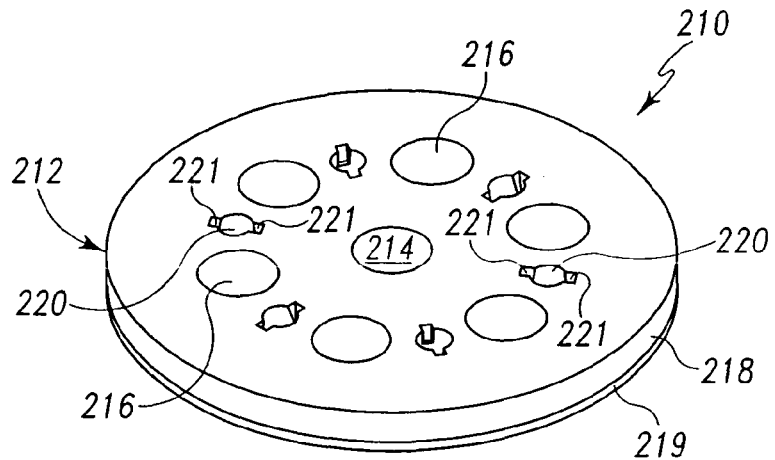
Fig. 27
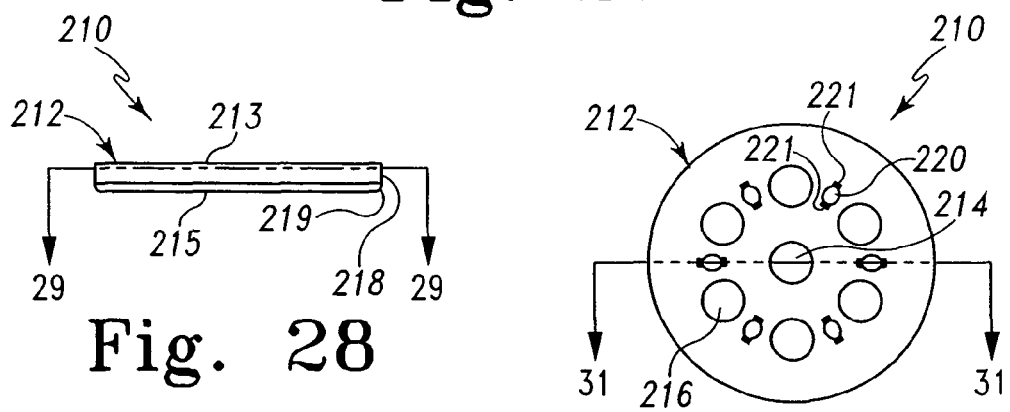
Fig. 28
Fig. 30
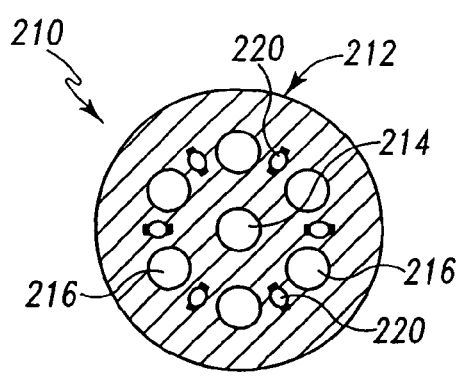
Fig. 29
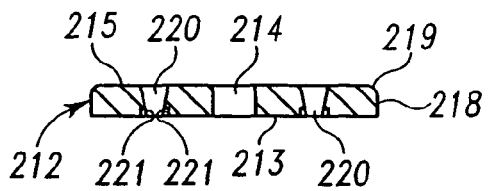
Fig. 31

IMPLANT DEVICE FOR CARTILAGE REGENERATION IN LOAD BEARING ARTICULATION REGIONS

FIELD OF THE INVENTION

The present invention relates to regeneration of cartilaginous tissue in load bearing regions and/or the tendency toward the resorption of subchondral bone and, more particularly, to an implant device for reducing the resorption of subchondral bone and thereby enhancing the regeneration of cartilaginous tissue in load bearing regions.

BACKGROUND OF THE INVENTION

Current techniques for repair and/or regeneration of articular lesions (autogenous chondrocyte transplantation and mosaicplasty) are generally considered to be unsatisfactory due to the fact that they require the harvesting of healthy tissue. As such, research has focused on the development of engineered devices that have the ability to stimulate conduction of hyaline-like tissue into the treated regions without using autogenous tissue sources. Such devices would be considered optimized scaffolds.

In vivo studies of articular cartilage regeneration typically utilize one of two animal models: the osteochondral defect and the full-thickness chondral defect. The osteochondral defect model is ideal for the generation of cartilage neotissue because access to the traumatized bone bed allows for recruitment of precursor cells, thereby enhancing the intrinsic wound healing response. In fact, osteochondral defects in the non-load-bearing areas heal spontaneously, albeit with fibrous tissue. The load-bearing region, however, is known to not heal spontaneously, and is characteristically accompanied by resorption of osseous walls and the formation of cavitary lesions.

In cases where load-bearing surfaces have been investigated with good outcomes, care has been taken not to compromise the subchondral plate (e.g. full-thickness chondral defect model). However, because the chondral defect model does not generate a hematopoietic wound healing response, spontaneous regeneration does not occur and thus cellular therapies are usually used in such circumstances. One notable exception is mosaicplasty. Mosaicplasty in femoral condyle (osteochondral) defects has been shown to maintain subchondral bone structure, further indicating that application of physiologic force plays a role in maintaining subchondral bone integrity.

Particularly, mosaicplasty utilizes cartilaginous plugs, but due to the need to harvest tissue from other sites, this technique is sometimes viewed as being suboptimal. Therefore, research has focused on the use of implant devices. In published U.S. patent application 2001/0039455A1, prosthetic bio-compatible polyurethane plugs that mimic the materials properties of the adjacent bone or cartilage tissue layer are described. These implants are intended to fill a cartilaginous defect with a non-resorbable cartilage-like material. However, application of load to subchondral bone is not described.

The use of load during cartilage regeneration has been described in several publications. In U.S. Pat. No. 6,530,956 a resorbable cage-like scaffold is described that consists of high porosity material seeded with transplanted chondrocytes. Loading is discussed with respect to the cage-like scaffold for withstanding and resisting compressive forces so that cell growing compartments of the cage-like scaffold are protected during tissue regeneration.

U.S. Pat. No. 6,511,511 describes a fiber-reinforced, porous, biodegradable implant in which the fibers act like struts to provide strength and stiffness to the scaffold and provide support for physiological loads. One particular embodiment is for osteochondral defects. Loading, however, is discussed only with respect to the device resisting high compressive stresses in the defect region thereby protecting the implant during tissue regeneration. In a similar manner, U.S. published U.S. patent application 2002/0119177 describes a method for reinforcing the mechanical and handling properties of a resorbable foam matrix using a mesh-like fabric. The primary purpose of the reinforcing mesh is to maintain the integrity of the foam component for surgical handling.

In published U.S. patent application 2003/0108587, an implantable device is described that can induce compression, tension, shear and other biomechanical forces to cells in order to induce cell proliferation and thus wound healing. The device is essentially a bioreactor that exerts micromechanical stimulation to cells through materials properties or application of external forces. This is taught, however, with respect to the regeneration of cartilage and not with respect to the healing of the subchondral bone as in the present invention.

Thus the need exists for a device for regeneration of articular cartilage that simultaneously applies load to subchondral bone.

It is thus an object of the present invention to provide an implant for cartilage regeneration in load-bearing regions.

It is thus another object of the present invention to provide an implant that applies a load from an articulating surface of a bone platform to an area of subchondral bone.

It is yet another object of the present invention to provide a load bearing implant for that reduces subchondral bone resorption.

SUMMARY OF THE INVENTION

In one form, the present invention is an implant device for applying a load to osteochondral defects. In another form, the present invention provides cartilage regeneration of osteochondral defects in load bearing regions. The implant may be fashioned as one integral device or may be fashioned as two or more portions that are attached to one another.

The implant includes an upper platform structure and a lower platform structure with a load transfer structure situated there between. A fixation structure may be included that aids in anchoring the implant to the defect area. The implant is comprised of a resorbable polymeric material or materials such as polyesters (polylactide, polyglycolide, polycaprolactone, polydioxanone, or combination thereof), co-polymers of resorbable polymers, or blends thereof.

The lower platform structure is preferably rigid (and alternatively the upper platform structure as well) and may be porous, or include pores or holes that allow for access to biologic elements (e.g. blood and bone marrow) from the subchondral bone. The implant also allows the receipt and retention of a resorbable scaffold or matrix material for cartilage regeneration in the defect area.

Particularly, in one form there is provided an implant device for an osteochondral defect. The implant device includes a first plate made of a resorbable biocompatible material, a second plate made of the resorbable biocompatible material, and a load transfer structure made of the resorbable biocompatible material and situated between the first plate and the second plate.

In another form, there is provided an implant device for an osteochondral defect. The implant device includes an upper plate made of a resorbable biocompatible polymer, a lower plate made of the resorbable biocompatible polymer and having a plurality of exposure bores, and a load transfer structure situated between the upper plate and the lower plate.

In yet another form, there is provided an implant for load bearing bone articulation surfaces. The implant includes an upper plate made of a bio-resorbable polymer and having an upper center bore, a lower plate made of the bio-resorbable polymer and having a lower center bore surrounded by a plurality of exposure bores, and a plurality of load transfer supports situated between a lower surface of the upper plate and an upper surface of the lower plate, the load transfer supports surrounding the upper and lower center bores.

BRIEF DESCRIPTION OF THE DRAWINGS

FIG. 16 is an enlarged top perspective view of an exemplary mating platform for the platform structure of FIG. 14;

FIG. 17 is a side view of the exemplary mating platform of FIG. 16;

FIG. 18 is a sectional view of the exemplary mating platform of FIG. 17 taken along line 18-18 thereof;

FIG. 19 is a top plan view of the exemplary mating platform of FIG. 16;

FIG. 20 is a sectional view of the exemplary mating platform of FIG. 19 taken along line 20-20 thereof;

FIG. 21 is an enlarged top perspective view of another exemplary mating platform for the platform structure of FIG. 14;

FIG. 22 is a top plan view of the exemplary mating platform of FIG. 21;

FIG. 23 is a side view of the exemplary mating platform of FIG. 21;

FIG. 24 is a sectional view of the exemplary mating platform of FIG. 23 taken along line 24-24 thereof;

FIG. 27 is an enlarged top perspective view of an exemplary mating platform for the platform structures of FIGS. 25 and/or 26;

FIG. 28 is a side view of the exemplary mating platform of FIG. 27;

FIG. 29 is a sectional view of the exemplary mating platform of FIG. 28 taken along line 29-29 thereof;

FIG. 30 is a top plan view of the exemplary mating platform of FIG. 27;

FIG. 31 is a sectional view of the exemplary mating platform of FIG. 30 taken along line 31-31 thereof.

DETAILED DESCRIPTION OF THE INVENTION

Figure 1:
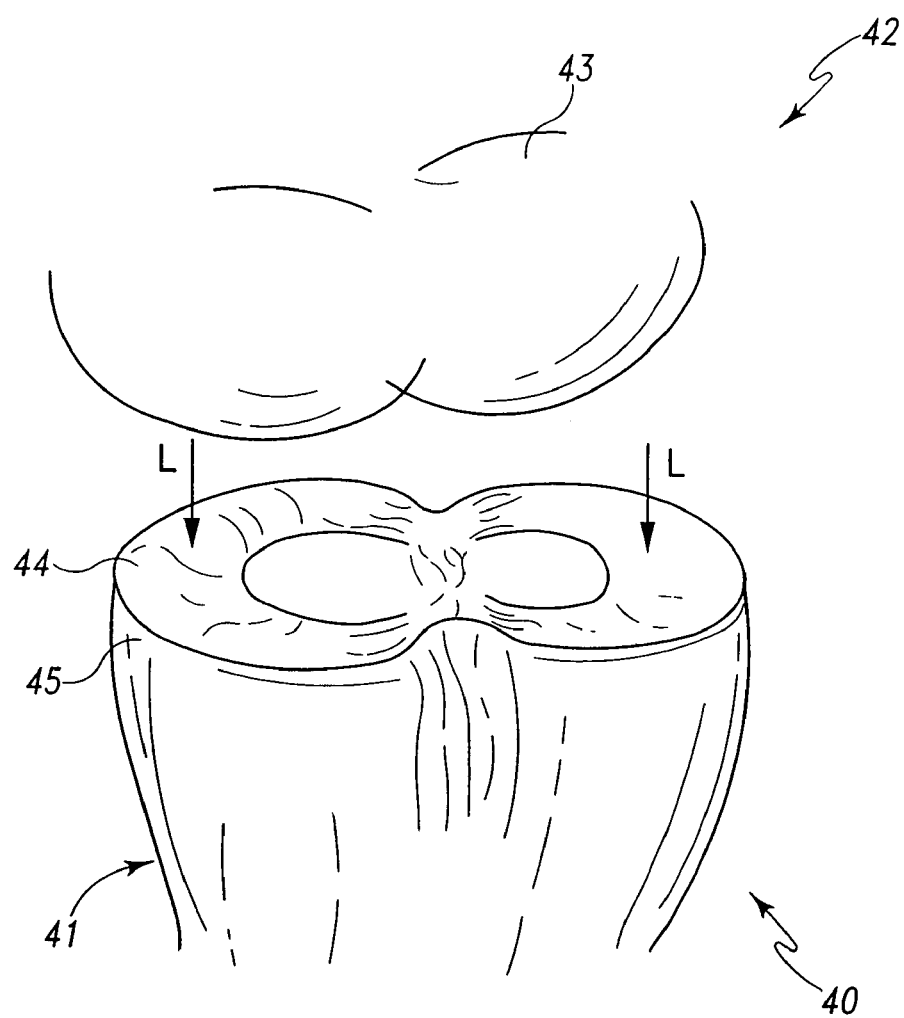
FIG. 1 is a diagrammatic view showing a tibial platform, representing an exemplary bone platform, being below the condyles of the femur; representing exemplary condyles.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents and alternatives falling within the spirit and scope of the invention as defined by the appended claims.

Referring now to FIG. 1, there is depicted a bone platform generally designated 40 being situated below condyles 42. The bone platform 40 of FIG. 1 is depicted as a tibial platform 40 of a tibia 41 while the condyles 42 are of a femur/knee. It should be appreciated that the tibial platform 40 and condyles 42 are representative of any similar bone platform. The tibial platform 40 supports a meniscus 44 that is over subchondral bone 45. The tibial platform 40 is assumed to have an osteochondral defect. The subject invention provides an implantable device for the osteochondral defect. The condyles 42 typically exert a load represented by arrows L onto the tibial platform 40. Particularly, the condyles 42 of the femur 43 exert physiological loading on the tibial platform 40 during normal joint use. The implant may be used for a medial femoral condylar (MFC) defect.

Figure 2:
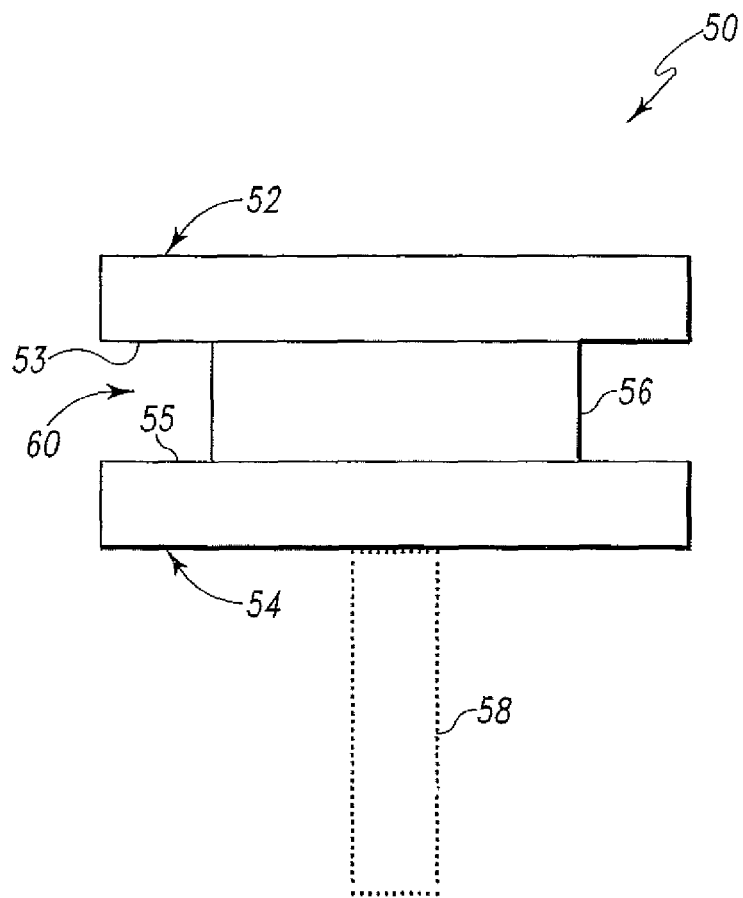
FIG. 2 is a block diagram illustrating an exemplary general form of a load bearing cartilage regeneration device in accordance with the principles of the subject invention.
Figure 3:
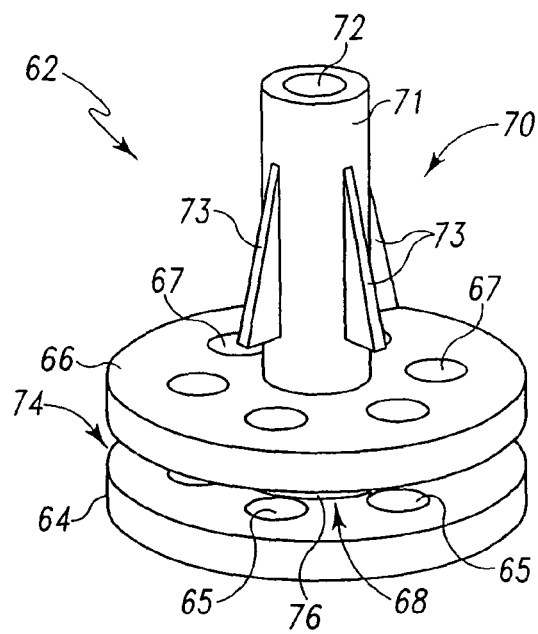
FIG. 3 is an enlarged perspective view of an exemplary embodiment of a load bearing cartilage regeneration device in accordance with the principles of the subject invention.
Figure 4:
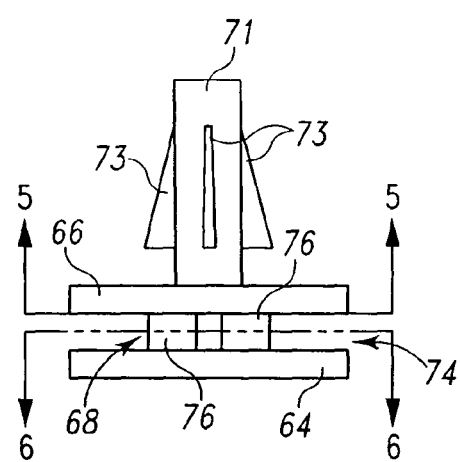
FIG. 4 is a side view of the load bearing cartilage regeneration device of FIG. 3.
Figure 5:
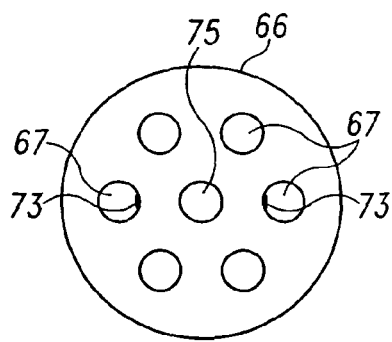
FIG. 5 is a sectional view of the load bearing cartilage regeneration device of FIG. 4 taken along line 5-5 thereof, particularly showing the lower platform thereof.
Figure 6:
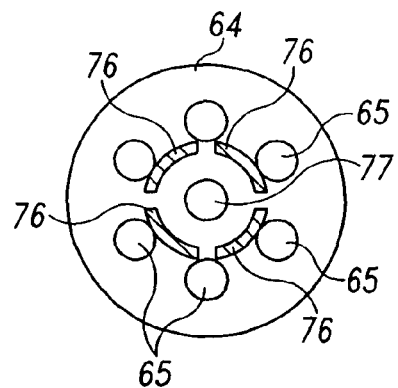
FIG. 6 is a sectional view of the load bearing cartilage regeneration device of FIG. 4 taken along line 6-6 thereof, particularly showing the upper platform thereof; including the load transferring structure.

Referring now to FIG. 2, there is depicted a block diagram of a load bearing subchondral bone resorption reduction and/or cartilage regeneration implant device generally designated 50 (and, hereinafter, "load bearing implant device", "implant" or the like) in accordance with the principles of the subject invention. The load bearing implant device 50 is representative of a general structure of the various embodiments of the present load bearing implant device shown and/or described herein.

The load bearing implant device 50 includes a first or upper platform, plate or the like 52 and a second or lower platform, plate or the like 54. It should be appreciated that the designations "first", "second", "upper" and "lower" are arbitrary. A load transfer structure 56 is interposed between the upper and lower platforms 52, 54. The load transfer structure 56 may take various forms but supports and transfers loading (e.g. physiological loading) exerted on the upper platform 52 to the lower platform 54. The lower platform 54 transfers the loading exerted thereon by the load transfer structure 56 to the substance of the area in which it is implanted (e.g. subchondral bone).

The load bearing implant device 50 is also shown with a fixation device 58. The fixation device 58 is depicted in dashed lines to indicate the optional nature thereof. Thus, the fixation device 58 is not a necessary portion of the implant 50. It is preferable, however, that the implant has some sort of fixation device. The fixation device 58 extends generally axially from the lower platform 54 and is utilized to aid in mounting the load bearing implant device 50 into the bone platform. The fixation device 58 may take various forms which are suitable for mounting the implant into bone (e.g., tibia 41 or condyle 43).

The upper and lower platforms 52, 54 are axially spaced from one another by the load transfer structure 56. An area 60 between the upper platform 52 and the lower platform 54 may be utilized to retain a scaffold, matrix or the like of a resorbable material that supports cartilage regeneration (e.g. a bio or artificial material). As such, the area 60 may be termed a scaffold or matrix retention area. The load bearing implant device 50 is designed such that the scaffold or matrix may be inserted before or after the device 50 has been implanted into the bone platform. Whether or not the scaffold or matrix is inserted before or after implantation may depend on the particular form of the load bearing implant device 50. Particularly, a one-piece implant design may have the scaffold before implantation thereof, while a two-piece implant may receive the scaffold after implantation thereof.

The load bearing implant device 50 is comprised of a bio-resorbable (resorbable) material. The resorbable material is preferably a poly(ester)s such as poly(lactide), poly(glycolide), poly(caprolactone), poly(dioxanone) or any combination, co-polymer or blend thereof. Other types of resorbable material(s) may also be used.

The lower platform 54 is preferably, but not necessarily, rigid yet porous. Such porosity may be effected by a porous material or the incorporation of bores, holes, pores or the like. As such the lower platform 54 allows the body access to biologic elements (bone and marrow) from the subchondral bone of the bone platform when the implant device 50 is implanted. The upper plate 52 is preferably likewise rigid, but may or may not be porous.

The load transfer structure 56 may be rigidly attached to both the upper plate 52 and the bottom plate 54 such that the load bearing implant device 50 is generally of a unitary or single piece structure. Particularly, the load transfer structure 56 adjoins the lower surface 53 of the upper plate 52 and the upper surface 55 of the lower plate 54. Alternatively, the load transfer structure 56 may be rigidly attached to the upper plate 52 and include a mechanism, structure or configuration that attaches or connects to the lower plate 54 via a mating mechanism, structure or configuration.

It should be appreciated that the attributes of the general load bearing implant device 50 as described above is applicable to the various particular embodiments of the load bearing implant device described hereinafter. Therefore, unless noted otherwise, the load bearing implant devices described hereinbelow, have and/or exhibit the same attributes as those described for the implant device 50.

Referring now to FIGS. 3-6, there is depicted an exemplary embodiment of a load bearing implant generally designated 62 in accordance with the present principles. Initially, it should be appreciated that the load bearing implant 62 is shown inverted 180° with respect to the load bearing implant device 50 of FIG. 3. This is for ease of depicting the optional fixation device portion 70 thereof.

The load bearing implant device 62 includes a first plate, platform or the like 64 having a plurality of exposure pores, holes, bores or the like 65. The plurality of exposure holes 65 (here six of which are shown) are arranged in an annular manner about the plate 64. The number and/or arrangement of the exposure holes 65 is generally arbitrary, but may be arranged to control the exposure of the defect area and scaffold to the normal joint environment. The greater the hole area (hole size and hole number), the greater the exposure. The plate 64 also includes a center hole or bore 76 that aids in insertion of the device 62 into the bone platform. 76 is the load-transferring mechanism, which in this case is a ring-shaped structure.

The load bearing implant device 62 also includes a second plate, platform or the like 66 having a plurality of exposure pores, holes, bores or the like 67. Again, the plurality of exposure holes 67 (here six of which are shown) are arranged in an annular manner about the plate 66. The number and/or arrangement of the holes 67 is generally arbitrary, but may be arranged to control the exposure of the defect area and scaffold to the normal joint environment. The greater the hole area (hole size and hole number), the greater the exposure. The plate 66 also includes a center hole or bore 75 that aids in insertion of the device 62 into the bone platform. The center hole 75 is intended to be just another bore.

The fixation device 70 comprises a tubular body 71 that axially projects from the second plate 66. The tubular body 71 has an axial bore 72 that is aligned coaxially with the center holes 75 and 77 of plates 66 and 64 respectively. A plurality of fins (anchors) 73 radially project from the tubular body 71. The fins 73 are fashioned as triangles. The fins may be embodied as ribs, barbs or the like and aid in the retention of the tubular body 71 in a bore in a defect area in the bone platform (see FIG. 32 and accompanying description). Of course, the fixation device 70, may takes other forms.

The load bearing implant device 62 of FIGS. 3-6 includes a load transfer structure 68. The load transfer structure 68 is embodied as a plurality (e.g. four as shown) of arc shaped or arcuate walls, portions, sections or the like 76. The arcuate walls 76 are situated about the center holes 75 and 77 of the plates 66 and 64. In this embodiment, the load transfer structure 68 is rigidly attached to both the first and second plates 64 and 66 to comprise a one-piece load bearing implant device.

The load bearing implant device 62 also defines a cartilage scaffold/matrix retention area 74 between the platforms 64 and 66. The retention area 74 receives and retains a cartilage scaffold/matrix such as is known in the art.

Figure 7:
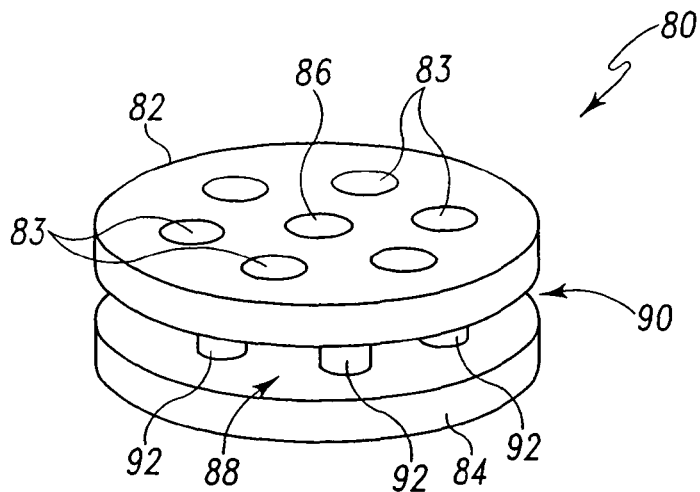
FIG. 7 is an enlarged perspective view of another exemplary embodiment of a load bearing cartilage regeneration device in accordance with the principles of the subject invention.
Figure 8:
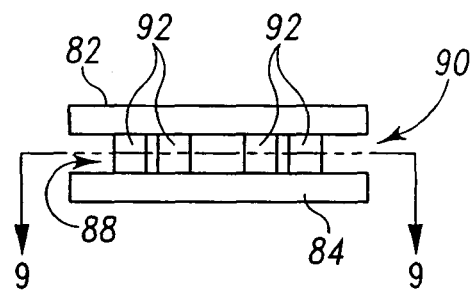
FIG. 8 is a side view of the load bearing cartilage regeneration device of FIG. 7.
Figure 9:
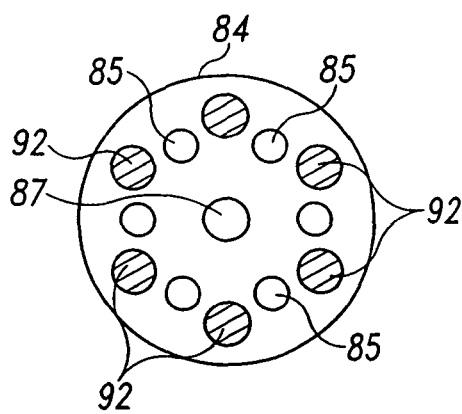
FIG. 9 is a sectional view of the load bearing cartilage regeneration device of FIG. 8 taken along line 9-9 thereof, particularly showing the lower platform thereof; including the load transferring structure.

Referring now to FIGS. 7-9, there is depicted an alternative embodiment of the present load bearing implant device generally designated 80. The load bearing implant device 80 is preferably made of the same material(s) as previously discussed. The load bearing implant device 80 has an upper or first plate or platform 82 and a lower or second plate or platform 84. The upper plate 82 includes a plurality of bores or holes 83 for defect area exposure in like manner to the load bearing implant device 62. The plurality of exposure bores 83 are arcuately spaced about a center bore 86. The lower plate includes a plurality of bores or holes 85 for defect area exposure in like manner as the upper plate 82. The plurality of bores 85 are arcuately spaced about the center bore 87. The number, size and/or arrangement of the bores 83 and 85 of the respective plates 82 and 84 may be modified as appropriate.

The load bearing implant device 80 also defines a cartilage scaffold/matrix retention area 90 between the platforms 82 and 84. The retention area 90 receives and retains the cartilage scaffold/matrix.

The load bearing implant device 80 of FIGS. 7-9 also includes a load transfer structure 88. The load transfer structure 88 is embodied as a plurality (e.g. six as shown) of columns, cylinders or the like 92. The columns walls 92 are situated about the center holes 86 and 87 of the plates 82 and 84. In this embodiment, the load transfer structure 88 is rigidly attached to both the first and second plates 82 and 84 to comprise a one-piece load bearing implant device. Placement of the load transfer columns 92 may vary as appropriate.

Figures 10, 11:
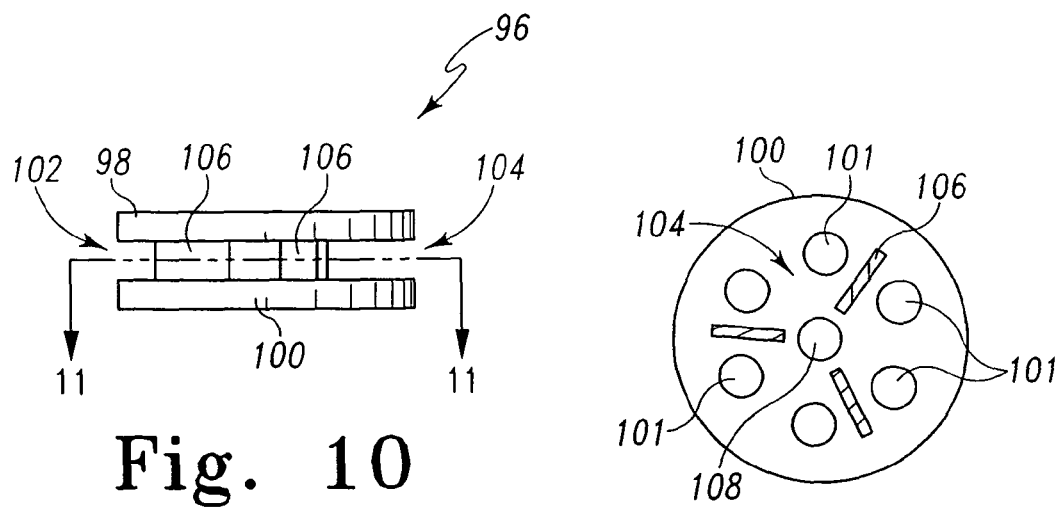
FIG. 10 is a side view of another exemplary embodiment of a load bearing cartilage regeneration device in accordance with the principles of the subject invention.
FIG. 11 is a sectional view of the load bearing cartilage regeneration device of FIG. 10 taken along line 11-11 thereof, particularly showing the lower platform thereof; including the load transferring structure.

Referring now to FIGS. 10 and 11, another alternative embodiment of a load bearing implant device is shown, generally designated 96. The load bearing implant device 80 is preferably made of the same material(s) as previously discussed. The load bearing implant device 96 includes an upper plate 98 and a lower plate 100. The upper plate 98 may or may not have exposure holes. The lower plate 100 includes a plurality of exposure bores 101 that are arcuately arranged in the plate about a center bore 108. The number, size and/or arrangement of the bores 101 of the plate 100 may be modified as appropriate.

The load bearing implant device 96 also defines a cartilage scaffold/matrix retention area 104 between the platforms 98 and 100. The retention area 104 receives and retains the cartilage scaffold/matrix.

The load bearing implant device 80 of FIGS. 10 and 11 includes a load transfer structure 102. The load transfer structure 102 is embodied as a plurality (e.g. three as shown) of rectangular walls, blocks or the like 106. The rectangular walls 92 extend radially from the center hole 108 of the plate 100. In this embodiment, the load transfer structure 102 is rigidly attached to both the first and second plates 98 and 100 to comprise a one-piece or unitary load bearing implant device.

Figures 12, 13:
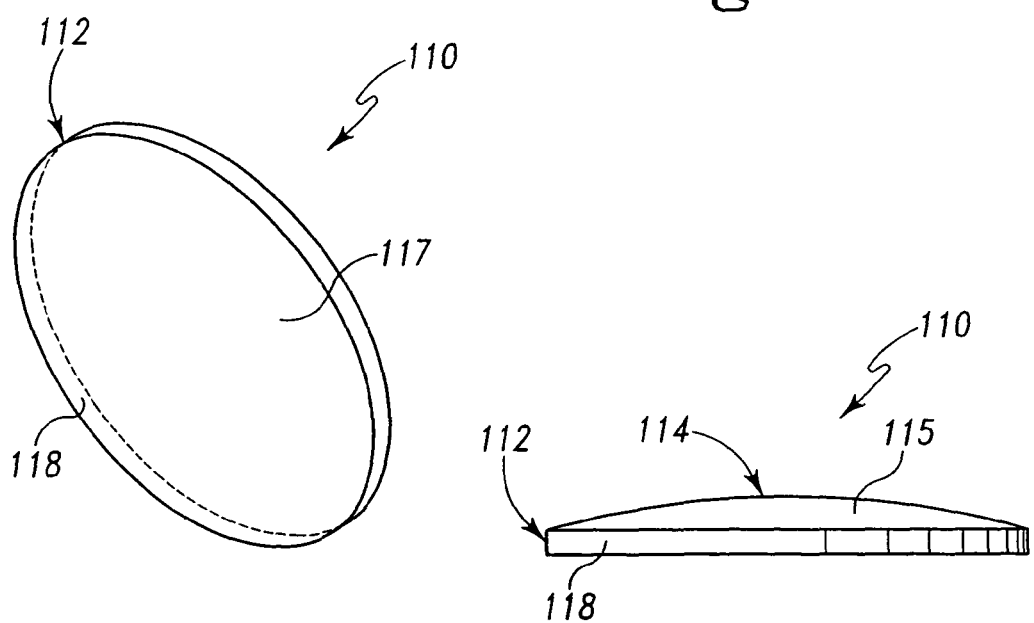
FIG. 12 is an enlarged bottom perspective view of an alternative upper platform utilizable with the various exemplary embodiments.
FIG. 13 is a side view of the upper platform of FIG. 12.

Referring now to FIGS. 12 and 13, an alternative embodiment or modification of an upper plate or platform is shown, generally designated 110. The upper plate 110 is preferably, but not necessarily, made of a polymeric material such as that described above. The upper plate 110 may be used in any of the implant embodiments shown herein. Particularly, the upper plate 110 may be used in place of the upper plate of any of the load bearing implant devices shown and/or described herein, or may be attached to the upper plate of any of the load bearing implant devices shown and/or described herein.

The plate 110 is defined by a body 112 having a domed portion 114 surrounded by a rim 118. The dome portion 114 defines a convex articulating surface 115 and thus a concave underside surface 117. The configuration of the modified top 110 provides a condylar-shaped articulating surface. Preferably, but not necessarily, the plate 110 does not include exposure holes. In lieu of such exposure holes, the plate 110 may be porous or solid.

As indicated above, one form of the present load bearing implant device is a two-piece design rather than a single piece design. It should be appreciated, however, that the load bearing implant device may be fashioned from more than two pieces if appropriate.

Figure 14:
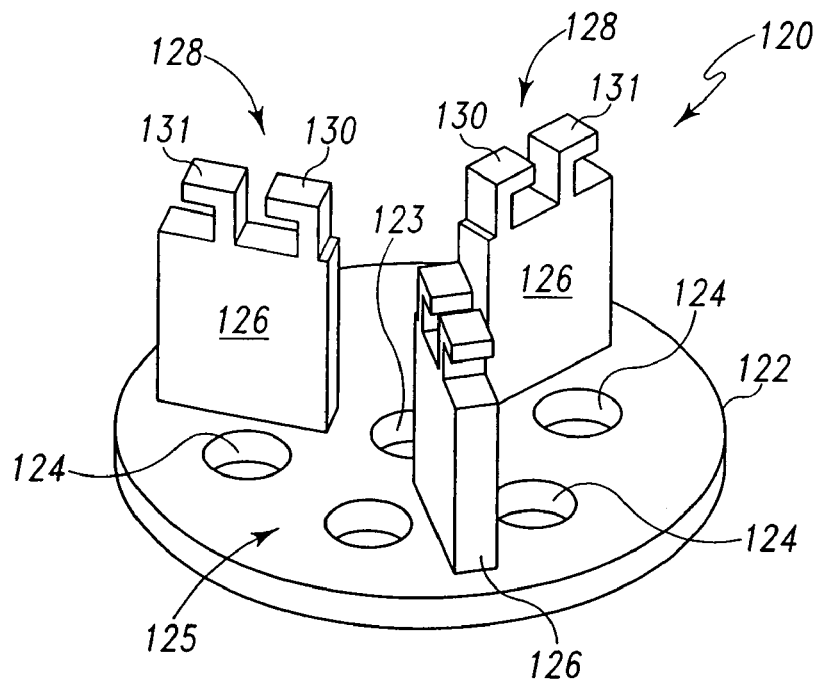
FIG. 14 is an enlarged top perspective view of an alternative embodiment of a platform having integral load transfer structures for a two-piece load bearing cartilage regeneration device, the load transfer structures designed to engage mating structures on a mating platform of the two-piece load bearing cartilage regeneration device such as that depicted in FIG. 16.
Figure 15:
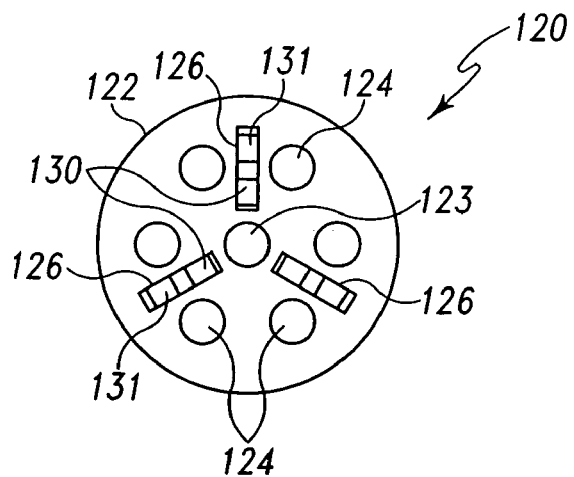
FIG. 15 is a top view of the platform of FIG. 14.

Referring now to FIGS. 14 and 15, an alternative embodiment of an upper platform structure is shown, generally designated 120, for a two-piece load bearing implant device. The upper platform structure 120 is again preferably made of a polymeric material as described above.

The upper platform structure 120 includes a plate 122 having a plurality of exposure holes or bores 124 arcuately arranged about a center bore 123. A load transfer structure 125 is integral with the plate 122 (i.e. a unitary structure). The load transfer structure 125 consists of a plurality (e.g., three as depicted) of rectangular blocks or walls 126 each having a mating structure 128. Of course, the load transfer structure 125 may consist of columns, rings, wedges or the like. The rectangular blocks extend radially outward from the center hole 123 toward the periphery of the plate 122. Each mating or attachment structure 128 includes first and second prongs 130 and 131. Each prong extends axially upward then radially outward to define a hook shape. The hook shape provides mating of the prongs with a configured lower plate as shown in FIGS. 16-20.

Referring now to FIGS. 16-20, there is depicted an exemplary lower platform structure generally designated 132 that may be used with the upper plate structure 120 of FIGS. 14-15. The upper and lower platform structures 120 and 132 provide a two-piece snap or press fit implant design. The lower plate structure 132 is defined by a platform or plate 134 having a plurality of exposure bores 136. The plurality of exposure bores 136 are arcuately provided about a center bore 137. Again, the size, number and/or arrangement of the exposure bores 136 are appropriate for the degree of exposure desired.

The plate 134 further defines a rim 141 having a tapered, beveled, or radiused edge 138. Extending radially outwardly from the center bore 137 is a plurality of rectangular bores 139 each of which has a ledge, shelf, protrusion, tab or the like 140 that extends therein as part of a connection, attachment or mating structure. Each bore and ledge combination is configured to receive a prong 130/131 of each load transfer structure 126. This provides a snap or press fit attachment or connection of the upper platform structure 120 with the lower platform structure 132.

It should be appreciated that the upper platform structure 120 is shown with two prongs 130/131 on each load transfer structure 126, while the receiving bores 139 of the lower plate structure 132 shows only one snap receiving structure 140 for clarity. In order to actually receive the upper platform structure onto the lower platform structure, there would either be only one prong on the load transfer structure of the upper platform structure, or there would be two receiving structures in the receiving bore.

The two-piece structure of the load bearing implant device defined by the upper platform structure 120 and the lower platform structure 132 allows for easier manufacture of the implant device. Moreover, once the lower platform structure 132 is implanted into the patient, the resorbable cartilage scaffold/matrix is situated thereon. The upper platform structure 120 is then situated onto the lower platform structure 120.

This gives the user the ability to select the type of resorbable scaffold/matrix material to be used with the load bearing implant device.

With the two-piece axial snap or press fit design of FIGS. 14-20, almost all of the force that will be exerted onto the implant device will be axial loading. As such, there the upper platform structure 120 will resist separation from the lower platform structure.

Referring now to FIGS. 21-24, there is depicted an alternative embodiment of a lower platform structure, generally designated 150, that may be used with the upper platform structure of FIGS. 14-15. The lower platform structure 150 provides a twist and lock configuration for receiving, attaching and retaining an upper platform structure. The lower platform structure 150 is preferably made of a resorbable polymeric material such as that described above. Moreover, the lower platform structure 150 is preferably a unitary piece.

The lower platform structure 150 is defined by a disk-shaped body, plate or the like 152 defining a first surface 153 and an opposite second surface 155. The plate 152 further defines an annular rim or periphery 157 having an annular taper, bevel or angled portion 158 transitioning between the rim 157 and the angled portion 158.

The plate 152 includes a plurality of exposure bores or holes 154 that are arranged about a center bore or hole 156. As with previous plates, the size, number and arrangement of the exposure holes 154 and/or the center hole 156, as well as whether to incorporate exposure holes or not, are subject to discretion depending on exposure factors. Additionally, the plate 152 has a plurality (e.g. three as shown) of configured bores 160 arranged about the center hole 156 and adjacent the exposure holes 154. Each configured bore 160 is adapted to receive and retain a mating structure (e.g., mating structure 128 of FIG. 14) of the load transfer structure (e.g., load transfer structure 125 of FIG. 14) of the upper platform (e.g., upper platform structure 120 of FIG. 14).

Each configured bore 160 has a projection, ledge, shelf or the like 162 projecting into the interior of the bore. The ledge 162 defines a retention mechanism for a prong of the upper platform structure. Each prong would require a separate ledge. Thus, to receive the two-pronged load transfer structure of the upper platform structure of FIGS. 14-15, each configured bore 160 would require two ledge structures. Once a prong is inserted into the configured bore, a twist thereof sets the ledge into under each prong. This motion, twist locks the upper plate platform into the lower plate platform.

Figure 25:
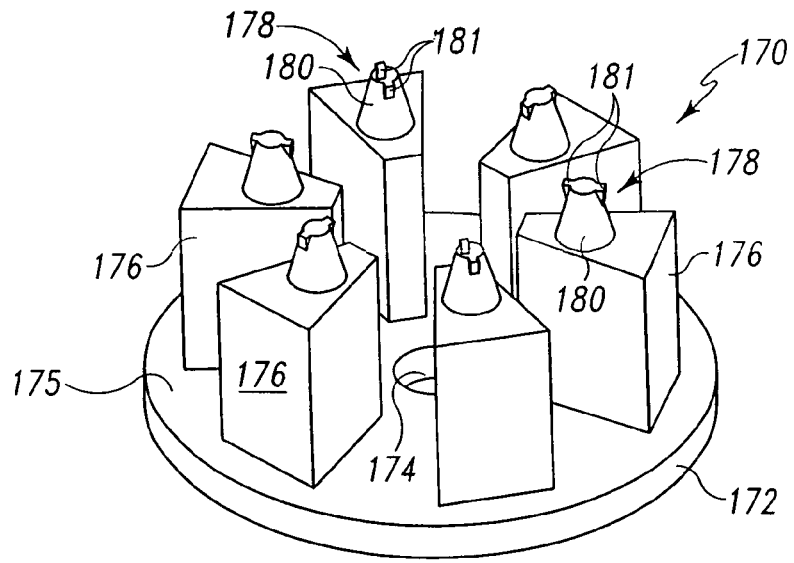
FIG. 25 is an enlarged top perspective view of another alternative embodiment of a platform having integral load transfer structures for a two-piece load bearing cartilage regeneration device, the load transfer structures designed to engage mating structures on a mating platform of the two-piece load bearing cartilage regeneration device.

In FIG. 25, there is depicted another exemplary embodiment of an upper platform structure generally designated 170. The upper platform structure 170 provides another example of one portion of a two-piece load bearing implant structure. Particularly, the upper platform structure 170 provides a structure that is retained onto a lower plate (see, e.g., plate 210 of FIGS. 27-31) in a press or snap fit manner.

The upper platform structure 170 is made of a polymeric material such as that described above and includes a plate 172 and a plurality of load transfer structures 176 that each axially extend from an upper surface 175 of the plate 172. The plate 172 also includes a center bore 174.

Each load transfer structure 176 is fashioned as a wedge having a mating structure 178 thereon. Each mating structure 178 is configured to be press fit received into a complementary lower platform structure or plate. Particularly, each mating structure 178 is here embodied as a truncated cone (cone section) 180 having two, diametrically opposed flanges 181. While only two flanges 181 are shown, the cone section 180 may support more or less flanges 181 as deemed appropriate.

Figure 26:
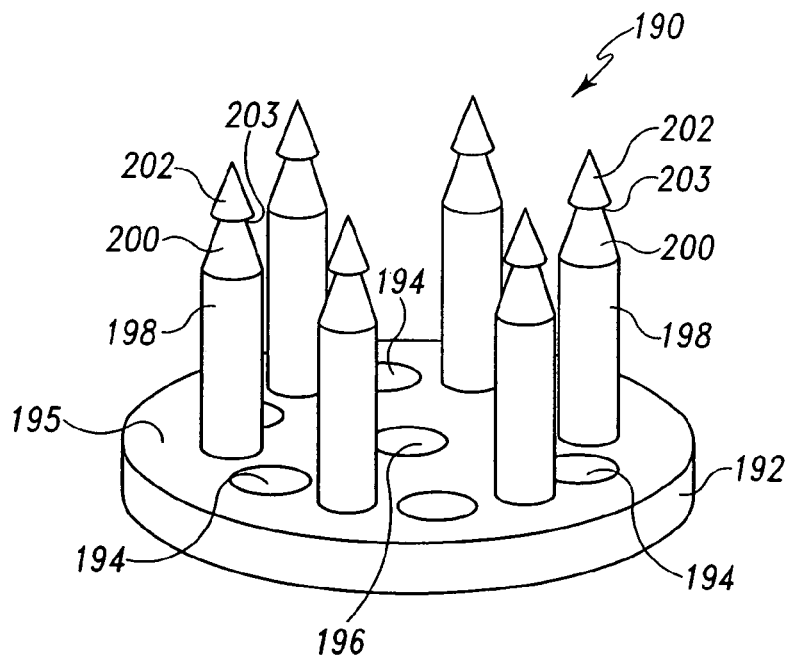
FIG. 26 is an enlarged top perspective view of yet another alternative embodiment of a platform having integral load transfer structures for a two-piece load bearing cartilage regeneration device, the load transfer structures designed to engage mating structures on a mating platform of the two-piece load bearing cartilage regeneration device.

Referring now to FIG. 26, there is shown another exemplary embodiment of an upper platform structure generally designated 190. The upper platform structure 190 provides another example of one portion of a two-piece load bearing implant structure. Particularly, the upper platform structure 190 provides a structure that is retained onto a lower plate (see, e.g., plate 210 of FIGS. 27-31) in a press or snap fit manner.

The upper platform structure 190 is made of a polymeric material such as that described above and includes a plate 192 having a plurality of exposure bores 194 arranged about a center hole 196. The plate 192 supports a plurality of load transfer structures 198 that each axially extend from an upper surface 195 of the plate 192. Each load transfer structure 198 is configured as a column, tube or the like having a first conical section or annular taper 200 and a second conical section, cone or tapered head 202. The cone 202 defines a skirt 203 that provides a manner of preventing the pulling out or reversal of the load transfer structure 198 when inserted into the corresponding lower platform structure. Cone 202 is intended to provide a mechanism for fixation into the subchondral bone.

Referring now to FIGS. 27-31, there is depicted an exemplary lower platform structure, generally designated 210, that can accommodate either one of the two exemplary upper platform structures 170 of FIG. 25 and 190 of FIG. 26. The lower platform structure 210 is defined by a body 212 in the shape of a plate, platform or the like that is fashioned from a suitable resorbable polymeric material such as that described above. The plate 212 defines an annular rim or periphery 218 between a first surface 213 and a second surface 215. Additionally, the plate 212 has an annular taper, bevel or angled surface 219 providing a transition between the rim 219 and the second surface 215.

The plate 212 further includes a plurality of exposure holes 216 that are arranged about a center bore 214. The size, number and/or arrangement of the exposure bores 216 are modifiable as necessary. Situated between each exposure bore 216 is a receiving, reception or mating bore 220 for a plurality of receiving bores 220. As best seen in FIG. 31, each receiving bore 220 is conical in shape and includes notches 221. The notches 221 allow for the reception of the flanges 181 of the load transfer structures 180 of the upper platform structure 170 of FIG. 25, and the reception of the skirt 203 of the upper platform structure 190 of FIG. 26.

Figure 32:
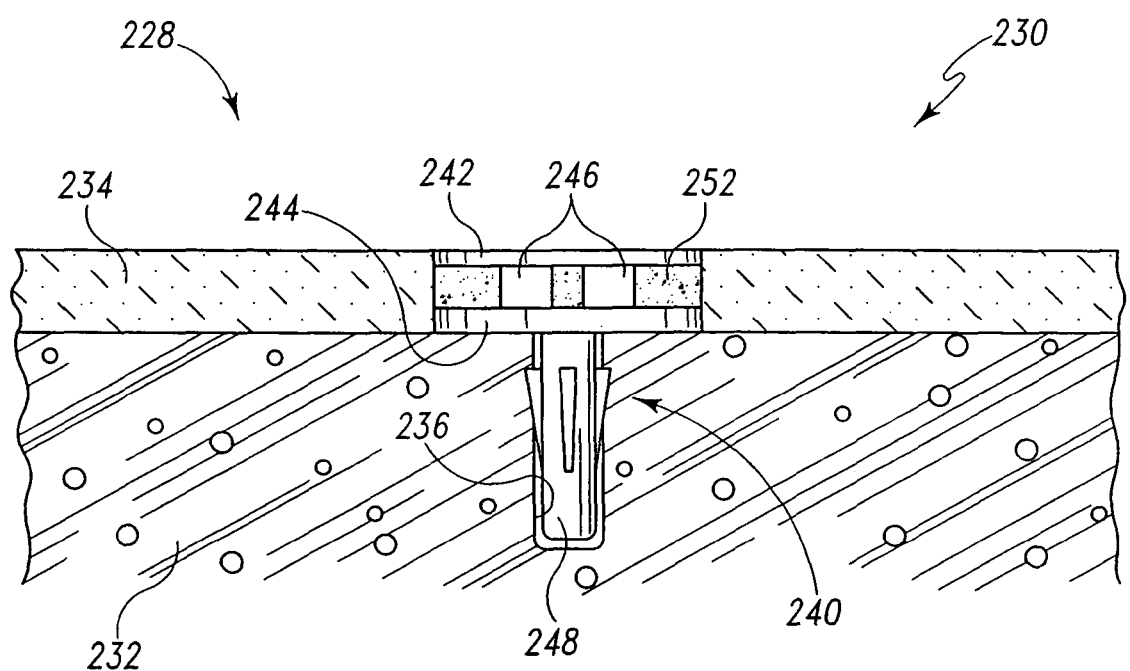
FIG. 32 is an enlarged side sectional view of a bone and cartilage platform depicting an exemplary load bearing cartilage regeneration device in accordance with the principles of the present invention implanted therein.

Referring lastly to FIG. 32, there is depicted an exemplary illustration depicting a load bearing implant device 240 fashioned in accordance with the principles of the subject invention implanted into a defect area 230 of a bone platform 228. A bore 236 has been formed in the subchondral bone 232 below the defect area in order to accommodate the fixation device 248 of the load bearing implant device 240.

The first or lower plate 244 of the load bearing implant device 240 is situated proximate and/or adjacent the subchondral bone 232 where the cartilage 234 meets the subchondral bone 232. The second or upper plate 242 of the load bearing implant device 240 is situated at the surface of the cartilage 234. A scaffold or matrix 252 is situated in between the two plates 242, 244 within the scaffold/matrix reception area of the load bearing implant device.

In each embodiment, load or pressure exerted onto the load bearing implant device structure (e.g., upper plate) at the articulating surface transfers the physiologic load to the load transfer structure. The load transfer structure then transfers the load to the device structure (e.g., lower plate) adjacent the defect area of the subchondral bone. This exerted pressure on the subchondral bone reduces the resorption of subchondral bone and/or the stimulation of subchondral bone synthesis. The load bearing implant device itself is resorbable, being preferably made of a resorbable polymeric material or materials. The subject invention also aids in the regeneration of cartilage tissue in load bearing regions with the ability to receive and retain a resorbable, cartilage regeneration scaffold or matrix (mesh, foam or the like).

What is claimed is:

1. An implant device for an osteochondral defect comprising:
   a first plate made of a resorbable biocompatible material;
   a second plate made of said resorbable biocompatible material, the second plate including a substantially flat plate surface extending substantially across one side of the second plate, an opposite substantially flat plate surface extending substantially across an opposite side of the second plate, and a plurality of radially extending elongated bores formed in the second plate, each of the radially extending elongated bores including a ledge positioned therein between the substantially flat plate surface and the opposite substantially flat plate surface; and
   a load transfer structure made of said resorbable biocompatible material and situated between said first plate and said second plate, said load transfer structure comprising a plurality of radially oriented elongated load transfer supports and at least one hook-shaped prong extending away from each of the elongated load transfer supports, each of the hook shaped prongs including a first portion extending outward from the associated elongated load transfer support and a second portion extending substantially perpendicular to the first portion in the radial direction, the second portion configured to engage the ledge of one of the radially extending bores.

2. The implant device of claim 1, wherein said resorbable biocompatible material is a polymer.

3. The implant device of claim 2, wherein said polymer comprises polyester.

4. The implant device of claim 1, wherein said second plate is porous.

5. The implant device of claim 1, wherein said load transfer structure is integral with said first plate, and receivable by said second plate.

6. The implant device of claim 1, further comprising a fixation device extending from said second plate.

* * * * *